US006187294B1

(12) United States Patent
Penner

(10) Patent No.: US 6,187,294 B1
(45) Date of Patent: Feb. 13, 2001

(54) TOPICAL ANESTHETIC PROPHYLAXIS COMPOSITION AND THE METHOD FOR USE THEREOF IN SCALING AND POLISHING TEETH

(76) Inventor: Russell Anthony Penner, 5359 Harvest Breeze Rd., Las Vegas, NV (US) 89118

( * ) Notice: Under 35 U.S.C. 154(b), the term of this patent shall be extended for 0 days.

(21) Appl. No.: 09/329,766

(22) Filed: Jun. 10, 1999

(51) Int. Cl.$^7$ ........................................................ A61K 7/16
(52) U.S. Cl. .............................................. 424/49; 433/216
(58) Field of Search .......................... 424/49–58; 433/216

(56) References Cited

U.S. PATENT DOCUMENTS

| | | | |
|---|---|---|---|
| 3,228,845 | * | 1/1966 | Najjar . |
| 3,574,859 | * | 4/1971 | Kosti . |
| 4,143,126 | * | 3/1979 | Gaffar . |
| 4,170,634 | * | 10/1979 | Cordon et al. . |
| 4,187,288 | * | 2/1980 | Cordon et al. . |
| 4,634,589 | * | 1/1987 | Scheller . |
| 4,913,894 | * | 4/1990 | Curtis et al. . |
| 5,124,143 | * | 6/1992 | Muhlemann et al. . |
| 5,192,802 | * | 3/1993 | Rencher . |
| 5,240,697 | * | 8/1993 | Norfleet et al. . |
| 5,266,304 | * | 11/1993 | Baffelli et al. . |
| 5,597,553 | * | 1/1997 | Baffelli et al. . |

FOREIGN PATENT DOCUMENTS

| | | | |
|---|---|---|---|
| 999238 | * | 11/1976 | (CA) . |
| 2143136 | * | 8/1996 | (CA) . |

OTHER PUBLICATIONS

Roghani et al Pediatric Dentistry 21(3): 197–200 10% Benzocaine 10% Lidocaine 5% Emla Cream Introral Topical Anastretis in Calddez, May 1999.*
Meechan et al ASDG JL Dentistry for Children 61 (4): 260–262 5% EMLA (Lidocaine/Prilocaine) 5% Lidolaine Ointment, Jul./Aug. 1994.*
Betts et al JL. Oral & Maxillo Facial Surgery 53(10): 1140–1144 Topical Viscors 2% Lidocaine Jelly Alleviates Pain in Extraction, Oct. 1995.*
Graser Oral Surgery, Oral Medicine Oral Pathology 58(1): 42–46 10% and 20% gels of benzocaine reduces intra oral pain, Jul. 1984.*

* cited by examiner

Primary Examiner—Shep K. Rose
(74) Attorney, Agent, or Firm—Jeffrey Weiss; Jeffrey D. Moy; Weiss & Moy, P.C.

(57) ABSTRACT

A topical anesthetic/prophylaxis paste is provided that is effective at removing extrinsic stains and plaque on the teeth and at reducing discomfort during scaling procedures thereon by delivery of an anesthetic into the gingival sulcus. The paste includes at least one topical anesthetic, either 5% Lidocaine or 20% Benzocaine, at least one humectant, preferably a Polyethylene glycol in the amount of about 28 to about 42 percent by weight, at least one abrasive agent, preferably pumice in the amount of about 55 to about 65 percent by weight, and at least one sweetener, preferably Saccharin sodium in the amount up to about three percent by weight. A method of delivering the topical anesthetic/prophylaxis paste into the sulcus by a low speed handpiece with a prophylaxis angle and rubber cup is also provided.

4 Claims, No Drawings

TOPICAL ANESTHETIC PROPHYLAXIS COMPOSITION AND THE METHOD FOR USE THEREOF IN SCALING AND POLISHING TEETH

FIELD OF THE INVENTION

This invention relates generally to dental compositions and, more specifically, to a topical anesthetic prophylaxis composition and the method for use thereof in scaling and polishing teeth.

BACKGROUND OF THE INVENTION

The techniques of dental hygiene or prophylaxis are applied directly to the teeth, the gingiva, and the gingiva sulcus, anatomical structures well known to the professional oral health practitioner. Generally, the gingiva includes the free gingiva. The gingival sulcus is the crevice or groove between the free gingiva and the tooth.

Optimum oral health may be substantially attained and maintained by complete and regular supragingival and subgingival scaling by a professional oral health practitioner such as a dental hygienist or dentist. After treatment by scaling or other periodontal therapy, the teeth are routinely polished. Polishing removes stains and plaque. Accompanied by the patient's therapeutic bacterial-plaque removal on a daily basis, inflammatory gingival and periodontal diseases may thus be substantially prevented.

Scaling is the basic treatment procedure by which supragingival and subgingival calculus (tartar) is removed from the surfaces of the teeth. Dental calculus, which is mineralized bacterial plaque, is a hard, tenacious mass that forms on the clinical crowns of the natural teeth and other dental appliances. The rough surface of the calculus holds the disease-producing bacteria close to the gingival tissue and perpetuates inflamed states. Calculus has thus long been considered to have an important role in the development, promotion and recurrence of gingival and periodontal infections. Accordingly, its removal by scaling is advantageous for oral health.

Scaling must be thorough to be effective. When calculus is left on the teeth, gingival irritation and inflammation can persist which may lead eventually to extensive rehabilitative treatment or loss of teeth.

The scaling procedure is well known to professional oral health practitioners. It may be done manually by a metal scaling instrument (commonly referred to as "scalers"). Ultrasonic and sonic instrumentation may be adjuncts to manual scaling. The principal objective is to remove the calculus with a minimum of trauma to the gingival tissue. Calculus is removed by scaling each tooth. Each scaling stroke overlaps the previous stroke as the scaler is positioned progressively along the area of the deposit.

Following scaling, the practitioner routinely polishes the teeth to remove plaque and extrinsic stains caused by, for example, tea, coffee, tobacco, etc. Polishing is generally done with an abrasive polishing agent with a stroke away from the gingiva and from the back of the mouth forward.

For those patients who experience discomfort and/or pain when undergoing the above procedures, an anesthetic may be administered before and/or while the procedures are being performed. A local anesthetic requiring an injection may be used but it requires a waiting period before being effective and requires the use of a needle that may increase the discomfort and/or pain felt by the patient. One alternative, nitrous oxide, requires specialized equipment making the hygienic procedures more expensive and more intimidating. In addition, some patients are not comfortable with using nitrous oxide. Moreover, the mask required to be worn by patients sedated by nitrous oxide may impede the dental practitioner. Both of these anesthetic remedies are relatively invasive to the patient. Although topical or surface anesthetics have been used for short-duration desensitization of the gingiva, their use has not been site-specific requiring more generalized application. Unfortunately, the topical anesthesia sometimes has to be reapplied if the practitioner does not timely reach the anesthetized area. Topical or surface anesthetics are drugs applied to the mucous membrane to produce a loss of sensation.

The anesthetizing, scaling, and polishing procedures as performed above take an extended amount of time for the practitioner to complete, all the while causing distress and anxiety to the patient such that the practitioner may worry about the patient and not be as thorough as possible in deference to the patient.

Accordingly, there has been a need for a novel composition and method that are substantially effective at substantially removing extrinsic stains and plaque. There is a still further need for a composition and method that increase the thoroughness in the completion of treatment. There is another need for a composition and method that increase the ease and smoothness of the dental hygiene procedures. There is still another need for a composition and method that increase the efficiency of the procedures resulting in a decrease in time required to complete the treatment. There is also a need for a composition and method that increase the patient's confidence in the professional oral health practitioner. There is also need for a composition and method that direct anesthesia to the actual sites being worked on. There is a further need for a composition and method that substantially increase the dental patient's comfort. Additionally, a composition and method are needed that require no specialized equipment that may be intimidating to an already discomforted patient. There is a further need for a composition and method that are not invasive. The present invention fulfills these needs and provides other related advantages.

SUMMARY OF THE INVENTION

In accordance with this invention, it is an object of this invention to provide a composition and method that are substantially effective at substantially removing extrinsic stains and plaque.

It is another object of this invention to provide a composition and method that increase the thoroughness in the completion of the dental hygiene treatment.

It is another object of this invention to provide a composition and method that increase the ease and smoothness of the dental hygiene procedures.

It is another object of this invention to provide a composition and method that increase the efficiency of the dental hygiene procedures resulting in a decrease in time required to complete the treatment.

It is another object of this invention to provide a composition and method that increase the patient's confidence in the professional oral health practitioner.

It is another object of this invention to provide a composition and method that direct anesthesia to the actual sites being worked on.

It is another object of this invention to provide a composition and method that substantially increase the dental patient's comfort.

It is another object of this invention to provide a composition and method that require no specialized equipment that may be intimidating to an already discomforted patient.

It is another object of this invention to provide a composition and method that are not invasive to the patient.

The present invention resides in an improved topical anesthetic prophylaxis composition and method for use thereof in scaling and polishing teeth. The composition comprises, generally, at least one topical anesthetic, at least one humectant, at least one abrasive agent, and at least one sweetener. The composition may also include at least one coloring and/or flavoring agent. A method of using the dental composition for substantially comfortable, painless, and time-saving scaling by polishing is also provided.

In a preferred form of the invention, the dental composition comprises, in combination, at least one topical anesthetic, about 28–42 percent by weight Polyethylene glycol, about 55–65 percent by weight pumice, and up to about three percent by weight sweetener. At least one flavoring may be added in an amount about 1 to about 5 percent by weight. At least one coloring may be added in an amount of up to about 1% by weight.

The at least one topical anesthetic includes 5% Lidocaine in an amount about one to about six percent by weight. The at least one topical anesthetic may be 20% Benzocaine in an amount about six to about 10% by weight.

Other features and advantages of the present invention will become apparent from the following more detailed description.

DETAILED DESCRIPTION OF THE PREFERRED EMBODIMENTS

The present invention is concerned with an improved dental composition for polishing which can increase comfort while the dental professional administers procedures for the prevention and treatment of gingival and periodontal diseases. The composition comprises, generally, at least one anesthetic agent, at least one abrasive agent, at least one humectant (also known as a base or carrier), and at least one sweetener. The composition may also include at least one coloring and/or flavoring agent. A method of using the dental composition for substantially comfortable, painless, and time-saving scaling by polishing is also provided.

In accordance with the present invention, the composition forms a paste although other forms may be made such as gels, ointments, solutions, troches or sprays.

The at least one anesthetic is selected from the group consisting of Lidocaine (5% by concentration) and Benzocaine (20% by concentration). The preferred percentages by weight for the Lidocaine are about one to about six percent and for Benzocaine, about six to about ten percent.

The humectants are used as the delivery vehicle for the anesthetic agent because most anesthetic agents are only slightly soluble in water. The preferred humectants are glycols such as Polyethylene glycol (PEG) 540 blend and 400. Polyethylene glycol (PEG) 540 blend and 400 are available, for example, from Union Carbide Corporation, Danbury, Conn. Other humectants may, of course, be used within the confines of the invention. For example, oils or alcohols may be used. The preferred percentages by weight of the PEG combination are about 28 to about 42% by weight. More specifically, the preferred range is about 34% to about 42% by weight PEG combination for the 5% Lidocaine plain (unflavored) paste and about 28% to about 35% for the 20% Benzocaine plain (unflavored) paste. The PEG combination for the mint-flavored Lidocaine and Benzocaine compositions is preferably about 30% to about 40% by weight.

The at least one abrasive agent preferably includes pumice. The preferred pumice is #2, a medium coarse pumice available from, for example, Kerr Corporation, Romulus, Mich. The number refers to the coarseness of the pumice. The medium coarse pumice may be blended with or substituted with finer or coarser grade pumices if it is determined that the patient may benefit therefrom. Other abrasive agents include, for example, silicon dioxide. The preferred percentage range for Pumice #2 is about 55 to about 65 percent by weight.

The sweetener preferably includes Saccharin sodium present in an amount about 0.2 g by weight. The preferred percentage of Saccharin sodium is up to about three percent by weight. Other of artificial, noncariogenic sweeteners may also be used.

The flavoring agents may be added to the composition to increase their palatability (taste) although the patient should be cautioned not to swallow the paste. For example, peppermint oil and/or spearmint oil may be added in a combined amount of about one to about 5 percent by weight for a mint flavor. Other flavors may, of course, be used. In the preferred embodiment, peppermint oil may be added in an amount about 1.2 percent by weight (0.3 g) and spearmint oil in an amount about 0.8 percent by weight (0.2 g).

The at least one coloring agent may be added to the composition. A preferred coloring agent includes a FD & C blue dye #1 solution, prepared by mixing one-fourth cup distilled water with 0.2 g FD & C dye. The preferred amount of FD & C blue solution is up to about 1 percent by weight.

The following are examples of preferred compositions. Each example shows preferred weight portions and percentages by weight:

|  | Lidocaine (plain) | Lidocaine (mint) |
|---|---|---|
| Weight (g) (by %): |  |  |
| Lidocaine USP: | 0.5 g (2%) | 0.5 g (2%) |
| PEG 540 blend: | 4.7 g (19%) | 4.5 g (18.1%) |
| PEG 400: | 4.6 g (18.5%) | 4.3 g (17.3%) |
| Pumice #2: | 14.8 g (59.7%) | 14.8 g (59.4%) |
| Saccharin Sodium: | 0.2 g (.8%) | 0.2 g (.8%) |
| Peppermint Oil: | — | 0.3 g (1.2%) |
| Spearmint Oil: | — | 0.2 g (.8%) |
| FD & C Blue #1: | — | 0.1 g (.4%) (4 drops) |
| Total Weight: | 24.8 g | 24.9 g |

|  | Benzocaine (plain) | Benzocaine (mint) |
|---|---|---|
| Weight (g) (by %): |  |  |
| Benzocaine USP: | 2.0 g (8.1%) | 2.0 g (8%) |
| PEG 540 Blend: | 4.0 g (16.1%) | 4.0 g (16%) |
| PEG 400: | 3.8 g (15.3%) | 3.3 g (13.3%) |
| Pumice #2: | 14.8 g (59.7%) | 14.8 g (59.4%) |
| Saccharin Sodium: | 0.2 g (.8%) | 0.2 g (.8%) |
| Peppermint Oil: | — | 0.3 g (1.2%) |
| Spearmint Oil: | — | 0.2 g (.8%) |
| FD&C Blue #1 | — | .1 g (.4%) (4 drops) |
| Total weight: | 24.8 g | 24.9 g |

The preparation of the composition involves mixing together under heat all the components except the pumice. The pumice is added last as a suspension.

As is well known in the art, the ratio of PEG 540 and PEG 400 may be adjusted to increase or decrease the viscosity of the paste. For example, if the percentage of PEG 540 is increased with a commensurate decrease in the percentage of PEG 400, the viscosity is increased. Conversely, if the percentage of PEG 540 blend is decreased with an increase in the percentage of PEG 400, the viscosity will be decreased.

In the method of the invention, the composition is delivered to the gingival sulcus by a low-speed handpiece such as is available from Midwest Dental (Chicago, Ill.). The handpiece is equipped with a standard prophylaxis angle. The prophylaxis angle is an attachment for the handpiece to which polishing devices such as a rubber cup are attached. The rubber cup is filled with the dental composition and the composition distributed over the tooth surfaces to be treated.

The procedure for distributing the composition is to establish a fulcrum point or finger rest to aid in balancing the handpiece. The rubber cup should almost be in contact with the tooth surface before activating the power source. The revolving rubber cup is placed at the cervical one-third (i.e. at the gum line) of the teeth being polished. Unlike the typical polishing stroke, the rubber cup is swept toward the gum tissue manipulating the rubber cup's flared edges subgingivally. The rotary movement of the rubber cup forces the composition into the gingival sulci. After packing the sulcus with the composition, the tooth is further polished with sweeping strokes away from the gum tissue (coronally). This polishing procedure is repeated with each tooth, refilling the cup as needed. As a result, the sulca epithelium and the free gingiva become numb so that scaling can then be done efficiently and in a shorter time than previously without substantial pain and discomfort.

It is preferred that the teeth in one arch be polished and scaled before polishing begins on another arch. This is because of the duration of the anesthetic effect. The hygienist may work in quadrants or even in sextants. Traditional polishing has usually been from the back of the mouth forward. However, when using the novel composition of the present invention, it is preferred to start in the anterior portion of the mouth to substantially limit the numbing effect. Although numbing of other areas of the mouth cannot be altogether eliminated, it may be substantially lessened by maintaining a dry field with conventional methods, for example, low evacuation (suction), gauzes, etc and by frequent rinses. The composition is particularly effective at substantially reducing pain and discomfort when such a dry field is maintained.

Frequent rinses are also necessary. Before rinsing, air should be blown into the sulcus. This will help deliver the composition into the sulcus. The area should then be rinsed off but no water directed into the sulcus. The composition will be removed during scaling, particularly with ultrasonic scalers.

From the foregoing, it is to be appreciated that the topical anesthetic prophylaxis paste is effective at substantially removing plaque and extrinsic stains on the teeth while delivering anesthetic effect to substantially decrease treatment time and substantially increase the patient's comfort during the subsequent scaling procedure.

Although a particular embodiment of the invention has been described in detail for purposes of illustration, various modifications may be made without departing from the spirit and scope of the invention. Accordingly, the invention is not to be limited, except as by the appended claims.

I claim:

1. A method of scaling and polishing a patient's teeth with an improved dental composition comprising the steps of:

providing a teeth cleaning composition;

wherein said teeth cleaning composition consists essentially of:

5% Lidocaine in an amount of about 2% percent by weight;

Polyethylene glycol 540 blend and Polyethylene glycol 400, the Polyethylene glycol 540 blend in an amount between about 18.1 and 19 percent by weight and the Polyethylene glycol 400 in an amount between about 17.3 and 18.5 percent by weight;

about 59 percent by weight Pumice; and about 0.8 percent by weight Saccharin Sodium;

preparing the teeth cleaning composition;

filling a rubber cup attached by a prophylaxis angle to a low speed handpiece with the teeth cleaning composition; and stroking the rubber cup on at least one tooth in the anterior portion of the patient's mouth first toward the gum tissue to pack the gingival sulcus with the teeth cleaning composition and then away from the gum tissue, moving from the anterior teeth to the posterior teeth.

2. The method of claim 1 the composition further including about 1.2% by weight Peppermint Oil, about 0.8% by weight Spearmint Oil, and about 0.4% by weight FD & C blue dye #1.

3. A method of scaling and polishing a patient's teeth with an improved dental composition comprising the steps of:

providing a teeth cleaning composition;

wherein said teeth cleaning composition consists essentially of:

20% Benzocaine in an amount of about 8 percent by weight;

Polyethylene glycol 540 blend and Polyethylene glycol 400, the Polyethylene glycol 540 blend in an amount about 16 percent by weight and the Polyethylene glycol 400 in an amount between about 13.3 and 15.3 percent by weight;

about 59 percent by weight Pumice; and about 0.8 percent by weight Saccharin Sodium;

preparing the teeth cleaning composition;

filling a rubber cup attached by a prophylaxis angle to a low speed handpiece with the teeth cleaning composition; and stroking the rubber cup on at least one tooth in the anterior portion of the patient's mouth first toward the gum tissue to pack the gingival sulcus with the teeth cleaning composition and then away from the gum tissue, moving from the anterior teeth to the posterior teeth.

4. The method of claim 3 the composition further including about 1.2% by weight Peppermint Oil, about 0.8% by weight Spearmint Oil, and about 0.4% by weight FD & C blue dye #1.

* * * * *